(12) United States Patent
Canal et al.

(10) Patent No.: US 9,675,564 B2
(45) Date of Patent: Jun. 13, 2017

(54) COMPOSITION BASED ON UBIDECARENONE

(71) Applicant: Asoltech Srl, San Dorligo della Valle (IT)

(72) Inventors: Tiziana Canal, Trieste (IT); Fulvio Fortuna, Trieste (IT); Elena Mencini, Piacenza (IT)

(73) Assignee: ASOLTECH S.R.L., San Dorligo Della Valle (IT)

( * ) Notice: Subject to any disclaimer, the term of this patent is extended or adjusted under 35 U.S.C. 154(b) by 250 days.

(21) Appl. No.: 14/362,219

(22) PCT Filed: Dec. 3, 2012

(86) PCT No.: PCT/IB2012/002565
§ 371 (c)(1),
(2) Date: Jun. 2, 2014

(87) PCT Pub. No.: WO2013/080028
PCT Pub. Date: Jun. 6, 2013

(65) Prior Publication Data
US 2014/0322189 A1    Oct. 30, 2014

(30) Foreign Application Priority Data
Dec. 2, 2011 (IT) .............................. UD2011A0196

(51) Int. Cl.
| | |
|---|---|
| *A61K 31/122* | (2006.01) |
| *A61K 8/35* | (2006.01) |
| *A61K 8/60* | (2006.01) |
| *A61Q 19/08* | (2006.01) |
| *A61K 9/14* | (2006.01) |
| *A61K 45/06* | (2006.01) |
| *A61K 31/07* | (2006.01) |
| *A61K 8/73* | (2006.01) |
| *A23L 33/10* | (2016.01) |
| *A23L 33/15* | (2016.01) |

(52) U.S. Cl.
CPC ............ *A61K 31/122* (2013.01); *A23L 33/10* (2016.08); *A23L 33/15* (2016.08); *A61K 8/355* (2013.01); *A61K 8/60* (2013.01); *A61K 8/732* (2013.01); *A61K 9/145* (2013.01); *A61K 9/146* (2013.01); *A61K 31/07* (2013.01); *A61K 45/06* (2013.01); *A61Q 19/08* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,202,818 B1 * | 3/2001 | Maucher | ............... | F16D 13/585 192/111.19 |
| 6,299,896 B1 * | 10/2001 | Cooper | ................... | A23L 1/302 424/400 |
| 7,342,097 B2 * | 3/2008 | Goddard | ............... | C07K 14/47 530/350 |
| 7,432,097 B2 * | 10/2008 | Short | .................... | A23K 20/189 424/94.6 |
| 2005/0002992 A1 * | 1/2005 | McCleary | ................ | A23L 1/24 424/439 |
| 2007/0202166 A1 | 8/2007 | Heuer et al. | | |
| 2007/0286902 A1 * | 12/2007 | Xie | ......................... | A61K 9/209 424/468 |
| 2008/0020018 A1 * | 1/2008 | Moodley | .............. | A61K 9/5073 424/433 |
| 2008/0038409 A1 * | 2/2008 | Nair | ......................... | A23G 1/56 426/73 |
| 2008/0248013 A1 | 10/2008 | Ikemoto et al. | | |
| 2009/0004170 A1 * | 1/2009 | Ikehara | ................ | A23K 1/1612 424/94.1 |
| 2009/0054530 A1 | 2/2009 | Parkhideh | | |
| 2009/0186009 A1 | 7/2009 | Sato et al. | | |

FOREIGN PATENT DOCUMENTS

| | | |
|---|---|---|
| CN | 101940564 A | 1/2011 |
| EP | 1 782 803 A1 | 5/2007 |
| GB | 2 402 334 A | 12/2004 |
| JP | 2005112744 A | 4/2005 |
| JP | 2005139122 A | 6/2005 |
| JP | 4601934 B2 * | 12/2010 |
| WO | 98/03170 A1 | 1/1998 |
| WO | 02/067864 A2 | 9/2002 |
| WO | 03/097012 A1 | 11/2003 |
| WO | 2007/009997 A1 | 1/2007 |
| WO | 2007/086689 A1 | 8/2007 |
| WO | 2012/063217 A1 | 5/2012 |

OTHER PUBLICATIONS

Ozaki, Aya et al. "Emulsification of Coenzyme Q10 Using Gum Arabic Increases Bioavailability in Rats and Human and Improves Food-Processing Suitability", J. Nutr. Sci Vitaminol, 2010, pp. 41-47, vol. 56.
Thanatuksorn, Pariya et al., "Improvement of the Oral Bioavailability of Coenzyme Q10 by Emulsification with Fats and Emulsifiers Used in the Food Industry", LWT—Food and Science Technology, 2009, pp. 385-390, vol. 42, Elsevier Ltd.
Chinese Office Action for Chinese Application No. 201280038888 dated Jun. 24, 2015, 6 pages.
Japanese Office Action for Japanese Application No. 2014543988 dated Jun. 19, 2015, 4 pages.
PCT Search Report dated Mar. 18, 2013 of Patent Application No. PCT/IB2012/002565 filed Dec. 3, 2012.
English translation and Chinese Office Action issued for related Chinese Application No. 201280068888.1 dated Oct. 15, 2015 (14 pages).
English translation and Korean Office Action issued for related Korean Application No. 10-2014-7018360 dated Nov. 12, 2015 (15 pages).
English translation and Korean Office Action issued for related Korean Application No. 10-2014-7018360 dated Feb. 12, 2016 (6 pages).
Canadian Office Action for Canadian Application No. 2,857,592 dated Feb. 4, 2016 (6 pages).

* cited by examiner

*Primary Examiner* — Thane Undrdahl
*Assistant Examiner* — Aaron J Kosar
(74) *Attorney, Agent, or Firm* — Lucas & Mercanti, LLP

(57) ABSTRACT

A composition based on ubidecarenone, or coenzyme Q10 or CoQ10, comprises CoQ10, one or more specific hydrophylic carriers selected from the maltodextrins class and one or more adjuvant agents selected from the sucrose-esters class.

10 Claims, 2 Drawing Sheets

COMPOSITION BASED ON UBIDECARENONE

RELATED APPLICATIONS

This application is a national phase application filed under 35 USC §371 of PCT Application No. PCT/IB2012/002565 with an International filing date of Dec. 3, 2012, which claims priority to Italian Application No. UD2011A000196, filed Dec. 2, 2011. Each of these applications is herein incorporated by reference in their entirety for all purposes.

FIELD OF THE INVENTION

The present invention concerns a composition based on ubidecarenone (hereafter called coenzyme Q10 or CoQ10), particularly, but not only, for use in the nutritional or dietary, cosmetic, therapeutic, pharmaceutical and veterinary fields.

BACKGROUND OF THE INVENTION

It is known that the coenzyme Q10, a yellow crystalline powder having a melting point of about 50° C., is a liposoluble substance similar to a vitamin that is found inside the mitochondrial inner membrane, in which it performs a function as an integrating part for transporting electrons in oxidative phosphorylation. For this reason high mytochondrial levels of Coenzyme Q10 increase the cell energy level and protect from oxidative stress. CoQ10 is used as a food supplement, anti-oxidant and in the treatment of cardiovascular disorders, such as angina pectoris, hypertension and cardiac congestive failure. CoQ10 is practically insoluble in water and poorly absorbed by the gastro-intestinal tract due to its high molecular weight and poor hydrosolubility: it is therefore a challenge in the development of a formulation for oral administration.

Many approaches are known for formulating CoQ10 in orally administrable forms.

At present, as CoQ10 food supplements, capsules are available on the market that are oil-based or filled with powder, and also tablet form. However, the oral dissolution and bio-availability of such formulations vary greatly.

For example, known formulation strategies include: solubilized systems with soy lecithin, micellar solutions of CoQ10 with castor oil hydrogenated polyossimetilene (60), lipidic microspheres prepared as emulsified soy oil with phospholipids from egg yolk, re-dispersible dry emulsions, complexation of CoQ12 with cyclodextrin, drug self-emulsifier transport systems and solubilized forms of CQ10 in a mixture of polysorbate 80 and medium chain triglycerides.

For example, the following are known: the scientific articles "Emulsification of coenzyme Q10 using gum arabic increases bioavailability in rats and humans and improves food-processing suitability" in J. Nutr. Sci, Vitaminol., 56, 41-47, 2010 and "Improvement of the oral bioavailability of coenzyme Q10 by emulsification with fats and emulsifiers used in the food industry" LWT—Food Science and Technology 42 (2009) 385-390 and the patent applications EP-A-1782803, GB-A-2402334, US-A-2007/202166, US-A-2008/248013, US-A-2009/054530, US-A-2009/186009, WO-A-02/067864, WO-A-98/03170 and WO-A-2007/086689.

However, for most of these formulations the dissolution profiles are not reported, either due to their oily nature and poor hydrosolubility, or due to the absence of a suitable dissolution mean. Furthermore, these approaches entail long and costly procedures.

In particular, WO-A-2007/086689 (WO'689) describes a composition obtained using ethanol and dichloromethane solvents and subsequent spray drying. The composition in WO'689 is formed by five compounds, that is, hydroxypropyl methylcellulose (HPMC) as hydrophilic polymer, a sucrose-ester of fatty acids with HLB=12, CoQ10, DL-alpha-tocopheryl acetate (vitamin E) and silicon dioxide (silica or siloid). WO-A-2007/086689 mentions the use of maltodextrins as a hydrophylic polymer, but without providing specific examples of possible compositions with the maltodextrins, or experimental data thereon.

Consequently, there is a great need in the field to supply a composition based on ubidecarenone and to perfect a method to prepare it, which on the one hand improves the solubility and dissolution of the CoQ10 and on the other hand can be made efficiently, quickly and economically.

To solve the technical problems concerning the preparation of compositions in fine powder form comprising substantially active principles with poor solubility in a water or organic environment, for a long time now a process of dry co-grinding has been studied and perfected, in which an active principle is included in a hydrophylic or hydrophobic carrier, depending on the chemical-physical characteristics of the active principle in question, in the presence of an auxiliary co-grinding substance which allows a drastic reduction in the co-grinding times with undeniable advantages for the stability of the active principle.

This process, described in the international application WO-A-03/097012 (WO'012), allows to obtain ternary compositions—which include active principle/carrier/auxiliary co-grinding substance—whose properties of solubility and dissolution are considerably better than the corresponding binary compositions of active principle/carrier. Subsequently, it was also found that, by applying the processes described above to anti-oxidant agents, including ubidecarenone, to obtain compositions in fine powder form that is easily dispersed in a water environment and possibly soluble therein, the compositions obtained showed a considerable increase in the anti-oxidant power given the same content of active principle in solution, as described in the international application WO-A-2007/009997 (WO'997).

WO-A-2012/063217 discloses compositions for treating phonatory and olfactory apparatus disorders and containing coenzyme Q10, maltodextrins, sugar esters, dibasic calcium phosphate, vitamin A and colloidal silica.

JP-A-2005112744 discloses a ubidecarenone tablet prepared by tableting small granules produced from 12 to 30 w/w % of ubidecarenone, an inner granule vehicle (lactose, sucroses, D-mannitol, xylitol, or the like), and a binder (maltodextrin, water-soluble cellulose, or the like) by a wet granulation method, a disintegrator such as carmellose calcium or cross carmellose sodium and a lubricant, such as sucrose fatty acid ester or magnesium stearate.

It is therefore a purpose of the present invention to obtain a composition in fine powder form based on ubidecarenone and comprising at least a specific hydrophylic carrier and at least an adjuvant agent in particular ratios, which solves the shortcomings of the state of the art, in particular showing a further increase in solubility compared with the compositions obtained in the state of the art and a corresponding increased capacity of penetration into the mitochondrial membrane by the composition.

It is also a purpose of the present invention to obtain the composition for use in treatments in the cosmetic, pharmaceutical, dietary and food and veterinary fields The Applicant has devised, tested and embodied the present invention to overcome the shortcomings of the state of the art and to obtain these and other purposes and advantages.

Unless otherwise defined, all the technical and scientific terms used here and hereafter have the same meaning as commonly understood by a person with ordinary experience in the field of the art to which the present invention belongs. Even if methods and materials similar or equivalent to those described here can be used in practice and in the trials of the present invention, the methods and materials are described hereafter as an example. In the event of conflict, the present application shall prevail, including its definitions. The materials, methods and examples have a purely illustrative purpose and shall not be understood restrictively.

The word "comprise" and variants of the word such as "comprises" and "comprising" are used here to indicate the inclusion of a clearly expressed whole or clearly expressed wholes but not the exclusion of any other whole or any other wholes, unless in the context or in use an exclusive interpretation of the word is required.

The word "consist" and variants of the word such as "consists" and "consisting" are used here to indicate the inclusion of a clearly expressed whole or clearly expressed wholes but not the exclusion of any other whole or any other wholes.

SUMMARY OF THE INVENTION

The present invention is set forth and characterized in the independent claims, while the dependent claims describe other characteristics of the invention or variants to the main inventive idea.

In accordance with the above purpose, forms of embodiment described here, which can be combined with other forms of embodiment described here, provide a composition based on ubidecarenone (hereafter coenzyme Q10 or CoQ10) which comprises or consists of CoQ10, one or more specific hydrophylic carriers selected from the class of maltodextrins and one or more adjuvant agents selected from the class of sucrose-esters, in particular weight/weight (w/w) ratios.

Here and hereafter, by the expression sucrose-ester, we mean an ester of sucrose with superior organic acids that is normally found as an odorless and flavorless white powder. Sucrose-ester normally has emulsifying properties.

The Applicant has found that the ternary composition according to the present invention, and in particular the CoQ10 contained therein, shows a considerable increase in solubility compared with the compositions obtained in the state of the art, and that such increase is also found in the capacity of the composition to penetrate the mitochondrial membrane. In other words, it has been found that in the ternary composition according to the present invention the CoQ10 is subjected to terclatration, that is, the CoQ10 is terclatrated, and is made more soluble in water. Therefore, the CoQ10 is more absorbable, thus improving its availability in the organism, given the same dose.

Here and hereafter, it is intended that the ternary composition according to the present invention only provides the above components CoQ10, maltodextrin(s) and sucrose-ester(s) as main components, without however excluding, in some variant forms of embodiment, that the composition according to the present invention can be associated with, put together with or mixed with other auxiliary components, for example to obtain a desired product, for example as a food integrator, for therapeutic pharmaceutical use, or veterinary use.

In some forms of embodiment, which can be combined with other forms of embodiment described here, the composition according to the present invention is a ternary composition and consists of three components or classes of components, that is, CoQ10, one or more specific hydrophylic carriers selected from the maltodextrins class and one or more adjuvant agents selected from the sucrose-esters class. Here and hereafter, the expression ternary composition means a composition according to the present invention that consists of CoQ10, one or more specific hydrophylic carriers selected from the maltodextrins class and one or more adjuvant agents selected from the sucrose-esters class.

In some forms of embodiment, which can be combined with other forms of embodiment described here, the composition according to the present invention consists of CoQ10, one or more specific hydrophylic carriers selected from the maltodextrins class and one or more adjuvant agents selected from the sucrose-esters class and can be used to make a formulation or product, being associated, put together or mixed with one or more substances, for example other active or auxiliary substances selected from a group comprising: vitamins, minerals or metals, such as magnesium, potassium, zinc, selenium, calcium, fluorine, phosphorus, complementary nutrients such as creatine, carnitine, gamma oryzanol, lipoic acid, choline, carnosine, phosphatidylserine, lutein, lycopene, resveratrol, other anti-oxidants, essential fatty acids omega-3, for example EPA and/or DHA, and omega-6, vegetable substances, extracts and/or preparations, such as for example extract of Blueberry, *Ginseng, Ginkgo biloba, Rhodiola rosea, Boswellia serrata*, yeast, intense sweeteners such as xylitrol, erythritol, mannitol, sorbitol, amino acids, branched or modified amino acids or other active or auxiliary substances.

The vitamins that can be used in the formulations that include the ternary composition according to the present invention can be selected, for example, from among one or more vitamins of a group that comprises: vitamin A, vitamins of the vitamin group B, including vitamins B1, B2, B3, (PP, niacin), B5, B6, B12, vitamin C, vitamin D, vitamin E, vitamin H.

In the case of active substances, it is intended that the composition according to the present invention is in association with, or mixed or put together with, said other substances in a formulation, whereas in the case of auxiliary substances it is intended that the ternary composition according to the present invention may comprise in addition said other substances.

One form of embodiment of the present invention provides a percentage in weight of CoQ10 comprised between 5% and 30% weight/weight.

Another form of embodiment of the present invention provides a percentage in weight of CoQ10 comprised between 7.5% and 20% weight/weight.

Another form of embodiment of the present invention provides a percentage in weight of CoQ10 comprised between 10% and 15% weight/weight.

One form of embodiment of the present invention provides a percentage in weight of one or more adjuvant agents selected from the sucrose-esters class comprised between 5% and 30% weight/weight.

Another form of embodiment of the present invention provides a percentage in weight of one or more adjuvant agents selected from the sucrose-esters class comprised between 7.5% and 20% weight/weight.

Another form of embodiment according to the present invention provides a percentage in weight of one or more adjuvant agents selected from the sucrose-esters class comprised between 10% and 15% weight/weight.

In some forms of embodiment, given the percentage in weight of CoQ10 and co-grinding adjuvant agent selected in the sucrose-esters class, the percentage in weight in the composition according to the present invention of the hydrophylic carrier selected in the maltodextrins class is provided to complete the 100% in weight.

In some forms of embodiment, the percentages in weight of CoQ10 and sucrose-ester in the composition according to the present invention are the same. In other forms of embodiment, the percentages in weight of CoQ10 and sucrose-ester in the composition according to the present invention are different from each other.

In some forms of embodiment, the sucrose-ester selected is one or more of saccharose monopalmitate, saccharose monostearate, saccharose dipalmatate, saccharose distearate, saccharose alchilate or mixtures of two or more of these.

It also comes within the spirit of the present invention to provide a method for the preparation of a composition based on ubidecarenone, or the coenzyme Q10 or CoQ10, which provides to use CoQ10, one or more specific hydrophylic carriers selected from the maltodextrins class and one or more adjuvant agents selected from the sucrose-esters class.

The composition according to the present invention can be obtained with techniques such as dry co-grinding, as described in applications WO'012 and WO'997, incorporated here in their entirety as a reference, or extrusion, or kneading or other.

In some forms of embodiment, a dry co-grinding can provide that an active principle, like CoQ10, is included in a hydrophylic carrier like the maltodextrins, in the presence of an auxiliary co-grinding substance, like sucrose-ester, which allows a drastic reduction in the co-grinding times with undeniable advantages for the stability of the active principle.

In one form of embodiment, given as a non-restrictive example of the field of protection of the present invention, the dry co-grinding is a particularly suitable technique for the present invention, and is mainly advantageous because it does not use solvents or cause any heating of the components. In this case, it is advantageous to co-grind together at the same time the three components of the composition: CoQ10, maltodextrin and sucrose-ester, compared to the separate co-grinding of the sucrose-ester with the binary system with the CoQ10 and maltodextrin co-ground. In fact, in this way the sucrose-ester has a more active role as co-grinding adjuvant. The co-grinding technique can also give advantages in terms of solubility and releasability of the active principle.

The composition in powder according to the present invention can be made up as such, or mixed with acceptable excipients and suitably formulated in any form suitable for oral administration, including solid forms such as powders, granules, sachets, stick packs, capsules, tablets with possible normal or controlled release, for example time- or pH-dependent, or filmed or gastro-protected, colon-specific or multi-layer release, chewing gum or sweets, or liquid forms such as syrups, drops, elixirs, solutions and suspensions in general.

In addition, the composition according to the present invention can be incorporated in other formulations such as creams, ointments, gels, pastes, water-based creams, emulsions, serums, face powders, sprays and suchlike, suppositories, vaginal suppositories, transdermal patches and suchlike, toothpastes, periodontal gels, mouthwashes.

The composition according to the present invention, made up as such or mixed with acceptable excipients and suitably formulated, can be used in any form whatsoever suitable for food and dietary integration.

Examples of active or auxiliary components or substances that can be associated, mixed or put together with the composition according to the present invention if used in food or dietary integration are included in a group comprising: choline or cytil choline, L-arginine, creatine, *Ginkgo biloba, Ginseng, Rhodiola rosea, Boswellia serrata*, extract of Blueberry, vitamins A, B1, B2, B3 (PP or niacin), B5, B6, B12, C, D, E, H, live yeast, magnesium, selenium, zinc, potassium, calcium.

A specific feature of the composition according to the present invention for use in food or dietary integration provides the adjuvant treatment in states of debility or fatigue, connected or not with specific illnesses.

Another specific feature of the composition according to the present invention for use in food or dietary integration provides the adjuvant treatment of balance disturbances and deafness and tinnitus.

Another specific feature of the composition according to the present invention for use in food or dietary integration provides the adjuvant treatment of dysphonia.

Furthermore, the composition in powder according to the present invention, made up as such or mixed with acceptable excipients and suitably formulated, can be used in any form suitable for cosmetic use.

A specific feature of the composition according to the present invention for cosmetic use provides an esthetic treatment of reparative and tissue degeneration processes.

Another specific feature of the composition according to the present invention for cosmetic use provides a treatment to prevent aging of the skin (anti-aging).

Another specific feature of the composition according to the present invention for cosmetic use provides an esthetic anti-wrinkling treatment.

Finally, the powdered composition according to the present invention made up as such or, once produced in its ternary form, mixed with acceptable excipients and suitably formulated, can be used in any form suitable for pharmaceutical use, possibly also for veterinary use.

Some forms of embodiment described here may provide a formulation that comprises the ternary composition according to the present invention and vitamins of the vitamin B group, including one or more of vitamins B1, B2, B3 (PP or niacin), B5, B6, B12, creatine, *Ginseng*, magnesium and potassium. This formulation can be provided for example for use in the treatment of psycho-physical stress connected for example to increased work or study activity, or states of fatigue connected (or not) to specific pathologies.

Some forms of embodiment described here may provide a formulation that comprises the ternary composition according to the present invention and choline, L-arginine, vitamins of the vitamin B group, including one or more of vitamins B1, B2, B3 (PP or niacin), B5, B6, B12, vitamin A, vitamin E, selenium, zinc, magnesium and *Ginkgo biloba*. This formulation can be provided for example as an adjuvant to prevent the progressive loss of hearing, in the case of tinnitus or other disturbances of the hearing.

Some forms of embodiment described here may provide a formulation that comprises the ternary composition according to the present invention and carnitine, carnosine, magnesium, zinc and potassium, vitamins B1, B12, C and E.

This formulation can be provided for example for use in maintaining normal cardiac function.

Some forms of embodiment described here may provide a formulation that comprises the ternary composition according to the present invention and lutein, extract of Blueberry, vitamins A and B12 and zinc. This formulation can be provided for example for use in maintaining normal capacity of sight.

Some forms of embodiment described here may provide a formulation that comprises the ternary composition according to the present invention and omega-3 (EPA, DHA), vitamins A, B3, B5, C and D, H, calcium, fluorine, phosphorus and magnesium and xylitol, with or without *Boswellia serrata*. This formulation can be provided for example for dental use, contributing to the normal maintenance of the teeth, mineralization maintenance and the normal function of the gums and can be useful for preventing gum retraction.

Some forms of embodiment described here may provide a formulation that comprises the ternary composition according to the present invention and vitamin A. This formulation can be provided for example as an adjuvant in the field of speech, in cases of fatigue of the laryngeal muscles and/or alteration of the voice or dysphonia.

DETAILED DESCRIPTION OF SOME FORMS OF EMBODIMENT

Figure 1:
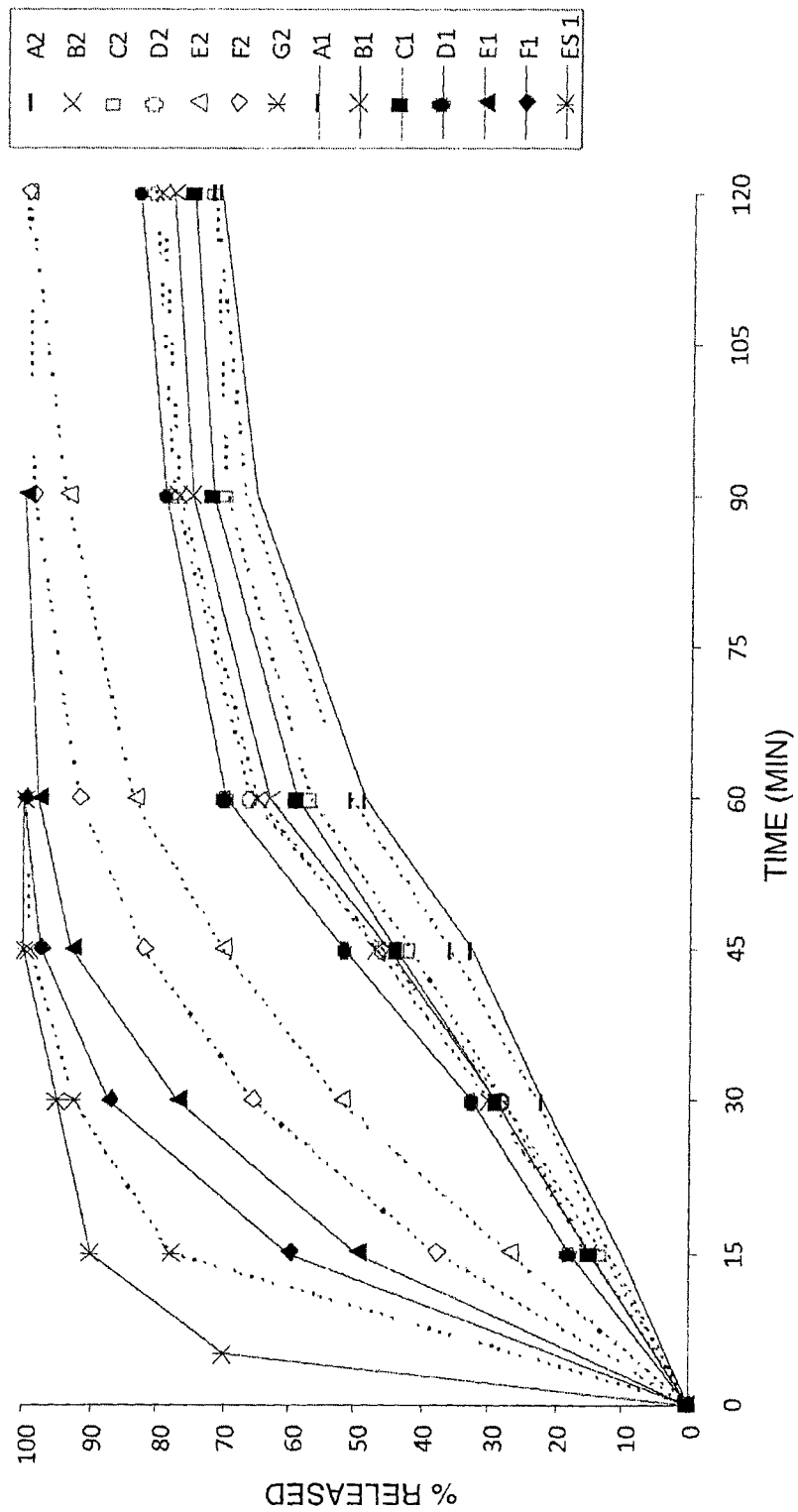
FIG. 1 is a graph illustrating a comparison of dissolution rates between ternary compositions configured in accordance with various embodiments of the present invention.

A specific form of embodiment of the present invention provides CoQ10 at 10% in weight, sucrose-ester at 10% in weight and maltodextrin at 80% in weight. This specific form of embodiment is also referred to as ternary composition of CoQ10/maltodextrin/sucrose-ester 1/8/1, or simply 1/8/1, referring to the ratios of weight to weight (w/w).

Another specific form of embodiment of the present invention provides CoQ10 at 15% in weight, sucrose-ester at 5% in weight and maltodextrin at 80% in weight. This specific form of embodiment is also referred to as ternary composition of CoQ10/maltodextrin/sucrose-ester 1.5/8/0.5, referring to the ratios of weight to weight (w/w).

A specific form of embodiment of the present invention provides CoQ10 at 0.5% in weight, sucrose-ester at 15% in weight and maltodextrin at 80% in weight. This specific form of embodiment is also referred to as ternary composition of CoQ10/maltodextrin/sucrose-ester 0.5/8/1.5, referring to the ratios of weight to weight (w/w).

Another specific form of embodiment of the present invention provides CoQ10 at 5% in weight, sucrose-ester at 5% in weight and maltodextrin at 90% in weight. This specific form of embodiment is also referred to as ternary composition of CoQ10/maltodextrin/sucrose-ester 0.5/9/0.5, referring to the ratios of weight to weight (w/w).

Another specific form of embodiment of the present invention provides CoQ10 at 15% in weight, sucrose-ester at 15% in weight and maltodextrin at 70% in weight. This specific form of embodiment is also referred to as ternary composition of CoQ10/maltodextrin/sucrose-ester 1.5/7/0.5, referring to the ratios of weight to weight (w/w).

Another specific form of embodiment of the present invention provides CoQ10 at 20% in weight, sucrose-ester at 20% in weight and maltodextrin at 60% in weight. This specific form of embodiment is also referred to as ternary composition of CoQ10/maltodextrin/sucrose-ester 2/6/2, referring to the ratios of weight to weight (w/w).

Another specific form of embodiment of the present invention provides CoQ10 at 25% in weight, sucrose-ester at 25% in weight and maltodextrin at 50% in weight. This specific form of embodiment is also referred to as ternary composition of CoQ10/maltodextrin/sucrose-ester 2.5/5/2.5, referring to the ratios of weight to weight (w/w).

Another specific form of embodiment of the present invention provides CoQ10 at 30% in weight, sucrose-ester at 20% in weight and maltodextrin at 50% in weight. This specific form of embodiment is also referred to as ternary composition of CoQ10/maltodextrin/sucrose-ester 3/5/2, referring to the ratios of weight to weight (w/w).

Another specific form of embodiment of the present invention provides CoQ10 at 20% in weight, sucrose-ester at 30% in weight and maltodextrin at 50% in weight. This specific form of embodiment is also referred to as ternary composition of CoQ10/maltodextrin/sucrose-ester 2/5/3, referring to the ratios of weight to weight (w/w).

Some forms of embodiment, which can be combined with other forms of embodiment described here, can provide to use sucrose-ester or mixtures of sucrose-esters having HLB value comprised between 14 and 16.

EXAMPLES

Example 1: Composition According to the Present Invention 1/8/1

Ternary Composition of Coenzyme Q10/Maltodextrin/Sucrose-Ester 1/8/1.

In some non-restrictive forms of embodiment, for the preparation of the ternary composition of this example, a co-grinding technique is adopted in which 15 g of a mixture in w/w ratio 1/8/1 of coenzyme Q10 (1.5 g), maltodextrin (12 g) and sucrose-ester (1.5 g), obtained for example using a mixer with a rotary body, are loaded into a jar of a planetary mill and subjected to mechanical-chemical activation for 30 minutes at a speed of 200 rpm. At the end of the process, the product in fine powder form is discharged and sieved. A ternary composite material coenzyme q10/maltodextrin/sucrose-ester is obtained in a w/w ratio of 1/8/1 with a coenzyme q10 titer of 10% in weight.

COMPARATIVE EXAMPLES

Example A (state of the art according to WO'997): ternary compositions of ubidecarenone/copovidone/glycine 1/8/1.

For the preparation of the ternary composition of this example, 15 g of a mixture in w/w ratio 1/8/1 of ubidecarenone (1.5 g), copovidone (12 g) and glycine (1.5 g), obtained using a mixer with a rotary body, are loaded into a jar of a planetary mill and subjected to mechanical-chemical activation in the same conditions as applied in Example 1. At the end of the process, the product in fine powder form is discharged and sieved. A ternary composite material ubidecarenone/copovidone/glycine is obtained in a w/w ratio of 1/8/1 with an ubidecarenone titer of 10%.

Example B (replacement of the carrier component of Example A by the carrier used in the present invention): ternary compositions of ubidecarenone/maltodextrin/glycine 1/8/1.

For the preparation of the ternary composition of this example, 15 g of a mixture in w/w ratio 1/8/1 of ubidecarenone (1.5 g), maltodextrin (12 g) and glycine (1.5 g), obtained using a mixer with a rotary body, are loaded into a jar of a planetary mill and subjected to mechanical-chemical activation in the same conditions as applied in Example 1. At the end of the process, the product in fine powder form is discharged and sieved. A ternary composite material ubidecarenone/maltodextrin/glycine is obtained in a w/w ratio of 1/8/1 with an ubidecarenone titer of 10%.

Example C (replacement of the ternarizing component of Example A by the ternary component used in the present invention): ternary compositions of ubidecarenone/copovidone/glycine 1/8/1.

For the preparation of the ternary composition of this example, 15 g of a mixture in w/w ratio 1/8/1 of ubidecarenone (1.5 g), copovidone (12 g) and sucrose-ester (1.5 g), obtained using a mixer with a rotary body, are loaded into a jar of a planetary mill and subjected to mechanical-chemical activation in the same conditions as applied in Example 1. At the end of the process, the product in fine powder form is discharged and sieved. A ternary composite material ubidecarenone/copovidone/sucrose-ester is obtained in a w/w ratio of 1/8/1 with an ubidecarenone titer of 10%.

Example D (effect of the emulsifier): binary compositions ubidecarenone/sucrose-ester 1/1.

For the preparation of the binary composition of this example, 15 g of a mixture in w/w ratio 1/1 of ubidecarenone (7.5 g), and sucrose-ester (7.5 g), obtained using a mixer with a rotary body, are loaded into a jar of a planetary mill and subjected to mechanical-chemical activation in the same conditions as applied in Example 1. At the end of the process, the product in fine powder form is discharged and sieved. A binary composite material ubidecarenone/sucrose-ester is obtained in a w/w ratio of 1/1.

Examples E for comparison with the state of the art according to WO'689:

We shall now present some examples for comparison (A1-F1-A2-G2) made according to the examples 27 and 28 in WO'689 and some variations of said examples intended to show the differences and advantages of the present invention both in terms of ternary composition consisting of ubidecarenone, sucrose-esters and maltodextrins with respect to the pentenary compositions used in WO'689, and also in terms of the techniques used, based on co-grinding, compared with the techniques with solvents and spray-drying as used in WO'689.

Hereafter the following abbreviations may be used: siloid=silicon dioxide or silica, mdx=maltodextrin(s), hpmc=hydroxypropyl methylcellulose, vit E=vitamin E or DL-alpha-tocopheryl acetate.

The experimental tests and comparisons carried out and discussed hereafter show that the ternary composition which consists of ubidecarenone (CoQ10), sucrose-ester(s) and maltodextrin(s) is better than the pentenary compositions of WO'689, irrespective of the technique used (co-grinding compared with spray-drying) and also that the maltodextrins class is better than hpmc as hydrophilic polymer carrier. It is clear from the following that the composition of the example 1 according to the present invention is in any case better than the other examples A1-F1, A2-G2 as proposed.

Examples of Comparison to Evaluate Co-Grinding

A1 Replication of Example 27 of WO'689 Using Co-Grinding

Compositions of Ubidecarenone/HPMC/Sucrose-Ester/Vitamin E/Siloid 33.3/31.2/33.3/0.1/2.

30 g of a mixture of ubidecarenone (9.99 g, 33.3%), HPMC (9.36 g, 31.2%) sucrose-ester (9.99 g, 33.3%), vitamin E (0.03 g, 0.1%) and siloid (0.6 g, 2%) obtained using a mixer with a rotary body, are loaded into a jar of a planetary mill and subjected to mechanical-chemical activation in the same conditions as applied in Example 1. At the end of the process, the product is discharged and sieved. A composite material ubidecarenone/hpmc/sucrose-ester/vitamin E/siloid is obtained with an ubidecarenone titer of 33.3%.

B1 Replication of Example 28 of WO'689 Using Co-Grinding

Compositions of Ubidecarenone/HPMC/Sucrose-Ester/Vitamin E/Silicon Dioxide 25/47.9/25/0.1/2.

30 g of a mixture of ubidecarenone (7.5 g, 25%), HPMC (14.37 g, 47.9%) sucrose-ester (7.5 g, 25%), vitamin E (0.03 g, 0.1%) and siloid (0.6 g, 2%) obtained using a mixer with a rotary body, are loaded into a jar of a planetary mill and subjected to mechanical-chemical activation in the same conditions as applied in Example 1. At the end of the process, the product is discharged and sieved. A composite material ubidecarenone/hpmc/sucrose-ester/vitamin E/siloid is obtained with an ubidecarenone titer of 25%.

C1 Comparison with Example 27 in WO'689 but without Vitamin E and Silicon Dioxide Ternary Compositions of Ubidecarenone/HPMC/Sucrose-Ester 33.3/33.3/33.3.

30 g of a mixture in a ratio w/w 1/1/1 of ubidecarenone (10 g, 33.3%), HPMC (10 g, 33.3%) and sucrose-ester (10 g, 33.3%), obtained using a mixer with a rotary body, are loaded into a jar of a planetary mill and subjected to mechanical-chemical activation in the same conditions as applied in Example 1. At the end of the process, the product is discharged and sieved. A composite ternary material ubidecarenone/hpmc/sucrose-ester is obtained with an ubidecarenone titer of 33%.

D1 Comparison with Example 28 in WO'689 but without Vitamin E and Silicon Dioxide Ternary Compositions of Ubidecarenone/HPMC/Sucrose-Ester 25/50/75.

30 g of a mixture of ubidecarenone (7.5 g, 25%), HPMC (15 g, 50%) and sucrose-ester (7.5 g, 25%), obtained using a mixer with a rotary body, are loaded into a jar of a planetary mill and subjected to mechanical-chemical activation in the same conditions as applied in Example 1. At the end of the process, the product is discharged and sieved. A composite ternary material ubidecarenone/HPMC/sucrose-ester is obtained with an ubidecarenone titer of 25%.

E1 Comparison with Example 27 in WO'689 but without Vitamin E and Silicon Dioxide and with Maltodextrin Instead of HPMC Ternary Compositions of Ubidecarenone/Maltodextrin/Sucrose-Ester 33.3/33.3/33.3.

30 g of a mixture of ubidecarenone (10 g, 33.3%), maltodextrin (10 g, 33.3%) and sucrose-ester (10 g, 33.3%), obtained using a mixer with a rotary body, are loaded into a jar of a planetary mill and subjected to mechanical-chemical activation in the same conditions as applied in Example 1. At the end of the process, the product is discharged and sieved. A composite ternary material ubidecarenone/maltodextrin/sucrose-ester is obtained with an ubidecarenone titer of 33%.

F1 Comparison with Example 28 in WO'689 but without Vitamin E and Silicon Dioxide and with Maltodextrin Instead of HPMC Ternary Compositions of Ubidecarenone/Maltodextrin/Sucrose-Ester 25/50/25.

30 g of a mixture of ubidecarenone (7.5 g, 25%), maltodextrin (15 g, 50%) and sucrose-ester (7.5 g, 25%), obtained using a mixer with a rotary body, are loaded into a jar of a planetary mill and subjected to mechanical-chemical activation in the same conditions as applied in Example 1. At the end of the process, the product is discharged and sieved. A composite ternary material ubidecarenone/maltodextrin/sucrose-ester is obtained with an ubidecarenone titer of 25%.

Examples of Comparison to Evaluate Co-Solubilization and Spray-Drying Technique

A2 Replication of Example 27 in WO'689

Compositions of Ubidecarenone/HPMC/Sucrose-Ester/Vitamin E/Silicon Dioxide 33.3/31.2/33.3/0.1/2

HPMC (9.36 g, 31.2%) is dispersed by stirring in 250 ml of ethanol to which the sucrose-ester (9.99 g, 33.3%) is added at ambient temperature. The ubidecarenone (9.9 g, 33.3%) is dissolved in 250 ml of methylene chloride and the solution added to the previous one. Then vitamin E (0.03 g, 0.1%) and silicon dioxide (0.6 g, 2%) are added and the whole is homogenized. The solution is spray-dried.

B2 Replication of Example 28 in WO'689

Compositions of Ubidecarenone/HPMC/Sucrose-Ester/Vitamin E/Silicon Dioxide 25/47.9/25/0.1/2.

HPMC (14.37 g, 47.9%) is dispersed by stirring in 400 ml of ethanol to which the sucrose-ester (7.5 g, 25%) is added at ambient temperature. The ubidecarenone (7.5 g, 25%) is dissolved in 400 ml of methylene chloride and the solution added to the previous one. Then vitamin E (0.03 g, 0.1%) and silicon dioxide (0.6 g, 2%) are added and the whole is homogenized. The solution is spray-dried.

C2 Example of Comparison Like Example 27 in WO'689 but without Vitamin E and Silicon Dioxide Ternary Compositions of Ubidecarenone/HPMC/Sucrose-Ester 33.3/33.3/33.3.

HPMC (10.0 g, 33.3%) is dispersed by stirring in 250 ml of ethanol to which the sucrose-ester (10.0 g, 33.3%) is added at ambient temperature. The ubidecarenone (10.0 g, 33.3%) is dissolved in 250 ml of methylene chloride and the solution added to the previous one. The solution is spray-dried.

D2 Example of Comparison Like Example 28 in WO'689 but without Vitamin E and Silicon Dioxide Ternary Compositions of Ubidecarenone/HPMC/Sucrose-Ester 25/50/75.

HPMC (15.0 g, 50%) is dispersed by stirring in 400 ml of ethanol to which the sucrose-ester (7.5 g, 25%) is added at ambient temperature. The ubidecarenone (7.5 g, 25%) is dissolved in 400 ml of methylene chloride and the solution added to the previous one. The solution is spray-dried.

E2 Example of Comparison Like Example 27 in WO'689 but without Vitamin E and Silicon Dioxide and with Maltodextrin Instead of HPMC Ternary Compositions of Ubidecarenone/Maltodextrin/Sucrose-Ester 33.3/33.3/33.3.

Maltodextrin (10.0 g, 33.3%) is dispersed by stirring in 250 ml of ethanol to which the sucrose-ester (10.0 g, 33.3%) is added at ambient temperature. The ubidecarenone (10.0 g, 33.3%) is dissolved in 250 ml of methylene chloride and the solution added to the previous one. The solution is spray-dried.

F2 Example of Comparison Like Example 28 in WO'689 but without Vitamin E and Silicon Dioxide and with Maltodextrin Instead of HPMC Ternary Compositions of Ubidecarenone/Maltodextrin/Sucrose-Ester 25/50/75.

Maltodextrin (15.0 g, 50%) is dispersed by stirring in 400 ml of ethanol to which the sucrose-ester (7.5 g, 25%) is added at ambient temperature. The ubidecarenone (7.5 g, 25%) is dissolved in 400 ml of methylene chloride and the solution added to the previous one. The solution is spray-dried.

G2 Example of Comparison Like Example 1 According to the Present Invention, but Using the Spray-Drying Technique Ternary Compositions of Ubidecarenone/Maltodextrin/Sucrose-Ester 1/8/1

Maltodextrin (24.0 g, 80%) is dispersed by stirring in 400 ml of ethanol to which the sucrose-ester (3 g, 10%) is added at ambient temperature. The ubidecarenone (3 g, 10%) is dissolved in 200 ml of methylene chloride and the solution added to the previous one. The solution is spray-dried.

Experimental Characterization of the Composition According to the Present Invention Solubility The solubility in water at 37° C. (physiological temperature) of the composition according to the present invention was compared with that of the compositions in the examples of comparison.

To analyze the solubility, an excess of composition according to the present invention is put in powdered form into water at 37° C., so as to have a sediment.

Verification is carried out after 1 hour and 24 hours (balanced) using the suitable analytical method (for example UV or HPLC spectrophotometry) of the maximum quantity of coenzyme Q10 that passes into the solution. The results are shown in the following Table 1, where the composition according to the present invention is shown as an example with that of Example 1.

TABLE 1

|  | Solubility 1 hour (µg/ml) | Solubility 24 hrs (µg/ml) | Increase over CoQ10 | |
|---|---|---|---|---|
|  |  |  | 1 hour | 24 hrs |
| CoQ10 | 1 | 4 | — | — |
| Example 1 | 280 | 330 | 280 | 83 |
| Example A | 50 | 150 | 50 | 38 |
| Example B | 3 | 22 | 3 | 5.5 |
| Example C | 40 | 110 | 40 | 27.5 |
| Example D | 4 | 18 | 3.5 | 4.5 |

Based on the results of Table 1, a greater solubility is found of the composition according to the present invention, in this case as in Example 1. This advantageous technical effect was not foreseeable in the state of the art based only on the fact that, for example, the carrier maltodextrin is more soluble in water than the previous carrier copovidone.

In fact, if we replace copovidone by maltodextrin (cf. the results of Example A and Example B), we have solubility after 24 hours equal to 22 µg/ml, therefore much lower than example A (50 µg/ml).

Furthermore, this advantageous technical effect in terms of the increase in solubility was also not foreseeable based on the emulsifying power of the sucrose-ester, since a binary co-ground composition, as in Example D, in the same w/w ratio as found in Example 1, has a solubility of 4 µg/ml at 1 hour and 18 µg/ml at 24 hours.

In the same way, the same applies if we replace the sucrose-ester with glycine in the composition in Example C compared with Example A.

Without being constrained by the theory, Applicant believes that the composition according to the present invention, reaching almost maximum solubility already after 1 hour (280 μg/ml compared with 330 μg/ml after 24 hours) compared with Example A (50 μg/ml compared with 150 μg/ml after 24 hours) where it is much lower, in vivo it will be more easily assimilated because it is readily available immediately, considering the mean transit time of the gastrointestinal tract.

Tables 2 and 3 show the results for solubility tests carried out as described above, between Examples E (A1-F1, A2-G2) described above and Example 1 according to the present invention.

TABLE 2

| EXAMPLE | SPRAY DRYING | | | | | | |
|---|---|---|---|---|---|---|---|
| | A2 | B2 | C2 | D2 | E2 | F2 | G2 |
| N. COMPONENTS | 5 | 5 | 3 | 3 | 3 | 3 | 3 |
| TITER IN Q10 (%), CARRIER | 33.3%, hpmc | 25%, hpmc | 33.3%, hpmc | 25%, hpmc | 33.3%, mdx | 25%, mdx | 10%, mdx |
| SOLUBILITY (μg/ml) | 70 | 105 | 80 | 110 | 140 | 160 | 200 |

TABLE 3

| EXAMPLE | CO-GRINDING | | | | | | |
|---|---|---|---|---|---|---|---|
| | A1 | B1 | C1 | D1 | E1 | F1 | Example 1 |
| COMPONENTS | 5 | 5 | 3 | 3 | 3 | 3 | 3 |
| TITER IN Q10 (%), CARRIER | 33.3%, hpmc | 25%, hpmc | 33.3%, hpmc | 25%, hpmc | 33.3%, mdx | 25%, mdx | 10%, mdx |
| SOLUBILITY (μg/ml) | 60 | 100 | 100 | 130 | 170 | 190 | 280 |

Considering the data shown above, the best composition, both in terms of co-grinding and spray-drying, is composition 1/8/1 of Example 1 according to the present invention.

Again according to the data shown above, the use of maltodextrin leads to better solubility results compared with hpmc. Without being constrained by the theory, the better performance of maltodextrin could be explained by a fine particle distribution of the components on the maltodextrin, which is soluble in water and therefore, when it comes into contact with it, helps the solubilization. On the contrary, hpmc not only gels but, given complete solubilization, when it is spray-dried it incorporates the CoQ10 more intimately and therefore releases it more slowly, also because of the gelled layer.

It should be noted that all the ternary preparations obtained through co-grinding are also better than their homologous preparations prepared through spray-drying: see F1 against F2, E1 against E2, D1 against D2 and C1 against C2.

It can be seen that, increasing the titer in CoQ10, although on the one hand the performance is slightly worse, since there is less carrier present, there is therefore less possibility for the CoQ10 to interact, the maltodextrin always behaves better than hpmc: see F2 against D2, E2 against C2 for co-grinding and F1 against D1, E1 against C1 for spray-drying. Furthermore, the results show that co-grinding is better than spray-drying: see F1 against F2, E1 against E2, D1 against D2 and C1 against C2.

Moreover, the performances of compositions with 5 components (pentenary) obtained by spray-drying are worse than those of the compositions with 3 components (ternary) obtained by spray-drying: see B2 against D2, A2 against C2. It can be deduced that the other two components, beyond the sucrose-ester, the hydrophylic carrier and the CoQ10, make the performance worse, and that the ternary composition is better irrespective of the spray-drying or co-grinding technique used.

From the data shown it also emerges that the performances of the compositions with 5 components obtained by spray-drying are better than the compositions with 5 components obtained by co-grinding: see A2 against A1 and B2 against B1. It can be deduced that the other two components, beyond the sucrose-ester, the hydrophylic carrier and the CoQ10, make the performance worse for co-grinding, and therefore it is important to choose the ternary compositions.

Finally, the performances of the ternary compositions obtained by co-grinding are better than the pentenary compositions obtained by co-grinding: see D1 against B1 and C1 against A1. In this case too it can be deduced that the other two components, beyond the sucrose-ester, the hydrophylic carrier and the CoQ10, make the performance worse for co-grinding, and therefore it is important to choose the ternary compositions.

Dissolution Rate Test (DRT)

Dissolution rate tests were carried out with the powders obtained in the examples A1-F1, A2-F2, weighed so as to use always 50 mg of Coenzyme Q10.

500 ml of pH buffer 1.2 were used, with an added 1% of Tween80 kept at T=37° C. and stirred at a speed of 50 rpm. Aliquots were taken at 15, 30, 60 and 120 minutes. For the DR test in Example 1, an aliquot was also taken at 5 minutes. Each aliquot was analyzed in HPLC under the following conditions:

Detector: UV at 275 nm
Column: Zorbax Extend 300 C18 or equivalent 4.6×150, 5 μm
T column: 25° C.
Mobile phase: ethanol/methanol 20/80
Flow: 2.0 ml/mn
TR: 8 min.

FIG. 1 shows the graphs for the DR tests carried out. The y-axis shows the percentage releasability of CoQ10 and the x-axis shows the time in minutes. The dotted lines show the examples made with spray-drying and the solid lines show the examples made with co-grinding.

The data shown above for the DR tests confirm what was said regarding the fact that the best composition, both in terms of co-grinding and spray-drying, is composition 1/8/1 of Example 1 according to the present invention. It is also clear that the compositions with hpmc are not able to release 100% of CoQ10 within the 120 minutes of the test, probably because hpmc tends to gel.

Absorption in Cardiomyoblasts

Despite the large number of clinical studies on the effects of Coenzyme Q10 supplementation, there are very few experimental data concerning the content of coenzyme Q10 in mitochondria and the cell energy condition after supplementation. Probably, controversial results of clinical and in vitro studies are mainly due to the bio-availability of the form of coenzyme Q10 used. For this reason, with reference to FIG. 2 attached, the capacity of the composition according to the present invention as per Example 1 (column III) and the composition in Example A (column II) for intracell penetration and the penetration of the mitochondrial membrane in cardiomyoblasts was also assessed, compared with Coenzyme Q10 as such (column I).

For this analysis, T67 cells of human astrocytoma and H9C2 cells from rats, deriving from the heart, were cultured in a Dulbecco's modified Eagle medium (DMEM), supplemented with 10% of fetal bovine serum (FBS), 100 Ul/ml of penicillin, 100 µg/ml of streptomycin and 40 µg/ml of gentamicin, in an atmosphere of 5% $CO_2$ at 37° C., with saturation humidity. The vitality of the cells and their number were measured using the exclusion method with Tripan blue (Lowry et al.). The mitochondria were isolated using known procedures (Chomyn, 1996). The cells treated were washed carefully with PBS before the extraction procedures. The extraction of the coenzyme Q10 from the isolated cells and mitochondria was performed as described by Takada et al. (Takada et al., 1984). The quantification of the coenzyme Q10 was done by means of HPLC analysis. From 50 to 100 µl of ethanol extract were subjected to chromatography on a C18 column (Kinetex, Phenomex, 2.6 µm, 100×4.6 mm), using a mobile phase that consists of an ethanol:water ratio of 97:3 v/v with a flow rate of 0.6 ml/min. The concentrations of coenzyme Q10 were obtained by comparing the peak areas with those of the standard solutions in at least three independent experiments.

Figure 2:
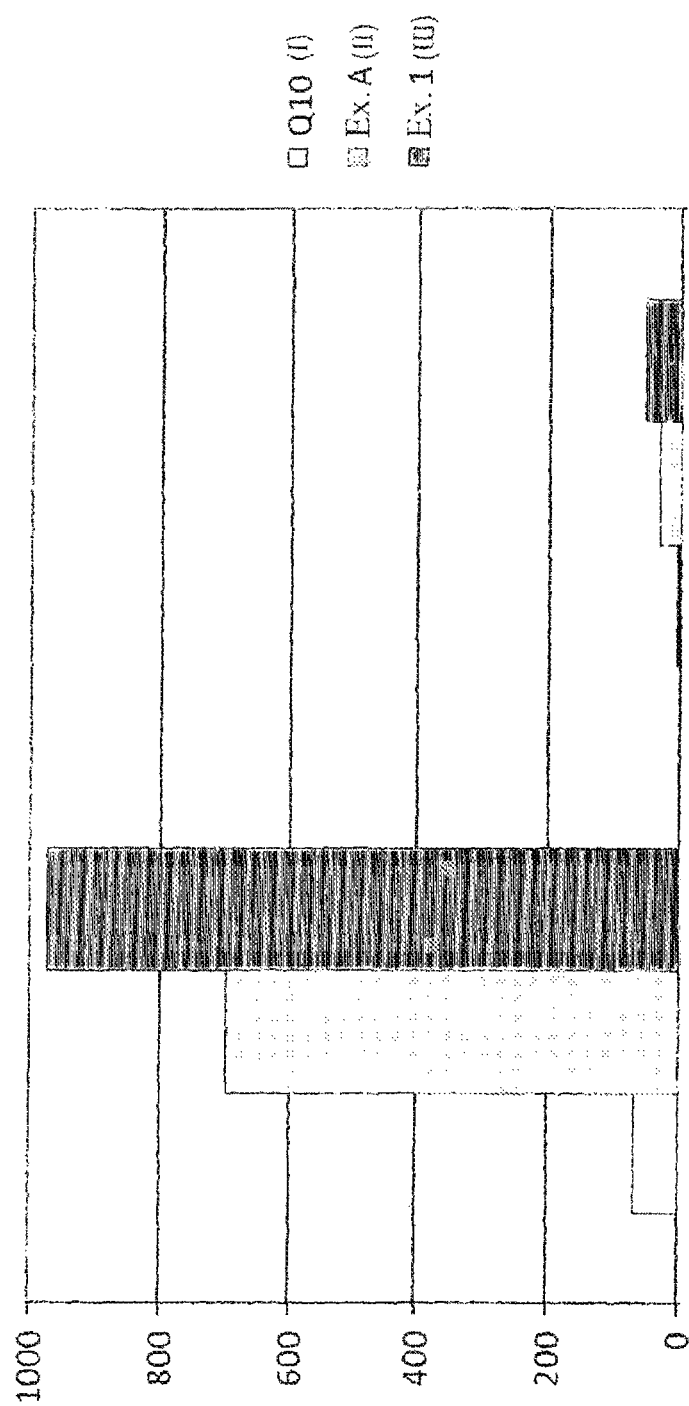
FIG. 2 is a graph illustrating a comparison of capacity for intracellular penetration of ternary compositions configured in accordance with various embodiments of the present invention.

FIG. 2 is a graph showing on the y-axis the increase in CoQ10 compared to the base value after a specific administration, and on the x-axis two groups of column graphs, in particular group A, relating to the increase tested on cells, and group B relating to the increase tested on mitochondria. In particular, FIG. 2 shows an increase in CoQ10 with respect to the base value after the administration of: CoQ10 as such (column I), composition according to the present invention as in Example 1 (column III) and composition as in Example A (column II):

In particular, an improvement can be seen in the passage of CoQ10 from whole cells to the mitochondria with the composition according to the present invention. In particular, with CoQ10 as such and with the composition as in Example A, 4% of CoQ10 passes from the whole cells to the mitochondria, whereas in Example 1 according to the present invention 5.3% of CoQ10 passes from the whole cells to the mitochondria, with a percentage increase of 32.5%.

The results also show that the intracellular content of Coenzyme Q10 correlates positively with the mitochondrial function and resistance to oxidative stress. The determination of the content of Coenzyme Q10 in lines of cultured cells after the administration of different compositions of Coenzyme Q10 has also shown that the most efficient formulation is the one according to the present invention as in Example 1 (column III). These results show that an adequate channeling of the coenzyme Q10 is important to ensure an appropriate cell uptake. The increased bio-availability also allows treatments with low doses of Coenzyme Q10 which allow to prevent an a-specific accumulation.

The invention claimed is:

1. A ternary composition based on ubidecarenone, consisting of ubidecarenone, one or more maltodextrin and one or more sucrose-ester, wherein
   the weight percentage of the ubidecarenone is between 10% and 33.3%;
   the weight percentage of the sucrose-ester is between 10% and 33.3%; and
   wherein the ubidecarenone, the maltodextrin and the sucrose-ester are combined by co-grinding in a dry state.

2. The ternary composition of claim 1, wherein maltodextrin is present in the ternary composition in a weight adjusted to bring the percent total weight of all components to 100%.

3. The ternary composition of claim 1, wherein the percentages of ubidecarenone and sucrose-esters in the composition are the same.

4. The ternary composition of claim 1, wherein the percentages of ubidecarenone and sucrose-esters in the composition are different.

5. The ternary composition of claim 1, wherein the sucrose-ester is selected from the group consisting of saccharose monopalmitate, saccharose monostearate, saccharose dipalmatate, saccharose distearate, saccharose alkylate, and mixtures thereof.

6. The ternary composition of claim 1, wherein the weight percentage of the ubidecarenone is 33.3%;
   and the weight percentage of the sucrose-ester is 33.3%.

7. The ternary composition of claim 1, wherein the weight percentage of the maltodextrin is between 33.3% to 80%.

8. The ternary composition of claim 1, wherein the weight percentage of the ubidecarenone is between 5% and 30%; and
   the weight percentage of the sucrose-ester is between 5% and 30%.

9. The ternary composition of claim 1, wherein the weight percentage of the ubidecarenone is between 10% and 15%; and
   the weight percentage of the sucrose-ester is between 10% and 15%.

10. A formulation comprising the ternary composition of claim 1, mixed with vitamin A.

* * * * *